(12) United States Patent
Spitler (10) Patent No.: US 10,064,657 B2
(45) Date of Patent: Sep. 4, 2018

(54) POLYAXIAL BONE ANCHOR INCORPORATING A THREADED BONE SCREW AND COMPRESSION SADDLE

(71) Applicant: FloSpine LLC, Boca Raton, FL (US)

(72) Inventor: James Q. Spitler, Orlando, FL (US)

(73) Assignee: FloSpine, LLC, Boca Raton, FL (US)

( * ) Notice: Subject to any disclaimer, the term of this patent is extended or adjusted under 35 U.S.C. 154(b) by 30 days.

(21) Appl. No.: 14/675,776

(22) Filed: Apr. 1, 2015

(65) Prior Publication Data
US 2015/0282843 A1 Oct. 8, 2015

Related U.S. Application Data

(60) Provisional application No. 61/974,154, filed on Apr. 2, 2014.

(51) Int. Cl.
*A61B 17/70* (2006.01)

(52) U.S. Cl.
CPC ...... *A61B 17/7037* (2013.01); *A61B 17/7082* (2013.01)

(58) Field of Classification Search
CPC ..................... A61B 17/70–17/7046
See application file for complete search history.

(56) References Cited

U.S. PATENT DOCUMENTS

| | | | | |
|---|---|---|---|---|
| 5,443,467 A * | 8/1995 | Biedermann | ...... | A61B 17/7032 606/308 |
| 5,882,350 A * | 3/1999 | Ralph | ................ | A61B 17/7032 606/278 |
| 8,092,502 B2 * | 1/2012 | Jackson | ............. | A61B 17/7037 606/266 |
| 9,277,938 B2 * | 3/2016 | Biedermann | .......... | A61B 17/70 |
| 2004/0102781 A1 * | 5/2004 | Jeon | .................... | A61B 17/7032 606/916 |
| 2004/0204711 A1 * | 10/2004 | Jackson | ............. | A61B 17/7035 606/308 |
| 2006/0247631 A1 * | 11/2006 | Ahn | .................... | A61B 17/7032 606/272 |
| 2007/0016200 A1 * | 1/2007 | Jackson | ............. | A61B 17/7005 623/17.16 |
| 2008/0200918 A1 * | 8/2008 | Spitler | ............... | A61B 17/7082 606/104 |

(Continued)

*Primary Examiner* — Eduardo C Robert
*Assistant Examiner* — Steven Cotroneo
(74) *Attorney, Agent, or Firm* — Clements Bernard Walker PLLC; Christopher L. Bernard (57) ABSTRACT

A polyaxial bone anchor assembly, comprising: a threaded screw portion comprising an externally threaded head end; a head body selectively disposed concentrically about the externally threaded head end of the threaded screw portion, wherein the head body defines an internally threaded hole in a bottom portion thereof; and an externally threaded compression saddle assembly selectively disposed within an interior portion of the head body and selectively engaging the externally threaded head end of the threaded screw portion; wherein the externally threaded compression saddle assembly and the externally threaded head end of the threaded screw portion are selectively disposed within the interior portion of the head body by engaging and passing through the internally threaded hole in the bottom portion of the head body.

4 Claims, 9 Drawing Sheets

(56) References Cited

U.S. PATENT DOCUMENTS

| | | | |
|---|---|---|---|
| 2009/0062866 A1* | 3/2009 | Jackson | A61B 17/7032 606/301 |
| 2009/0163962 A1* | 6/2009 | Dauster | A61B 17/7032 606/305 |
| 2011/0160778 A1* | 6/2011 | Elsbury | A61B 17/7037 606/305 |
| 2011/0190822 A1* | 8/2011 | Spitler | A61B 17/70 606/264 |
| 2014/0214084 A1* | 7/2014 | Jackson | A61B 17/7037 606/270 |
| 2015/0080960 A1* | 3/2015 | Biedermann | A61B 17/7037 606/278 |

* cited by examiner

POLYAXIAL BONE ANCHOR INCORPORATING A THREADED BONE SCREW AND COMPRESSION SADDLE

CROSS-REFERENCE TO RELATED APPLICATION

The present patent application/patent claims the benefit of priority of U.S. Provisional Patent Application No. 61/974,154, filed on Apr. 2, 2014, and entitled "THREADED BONE SHANK AND COMPRESSION MEMBER FOR USE IN A POLYAXIAL BONE ANCHOR," the contents of which are incorporated in full by reference herein.

FIELD OF THE INVENTION

The present invention relates generally to a polyaxial bone anchor, or pedicle screw, for the stabilization and fixation of bones, such as vertebrae of the spine. More specifically, the present invention relates to a polyaxial bone anchor, or pedicle screw, that incorporates a threaded bone screw and compression saddle, such that the polyaxial bone anchor, or pedicle screw, can be placed in either a pre-assembled configuration or a substantially disassembled configuration.

BACKGROUND OF THE INVENTION

A variety of conventional pedicle screws are known to those of ordinary skill in the art. These pedicle screws typically consist of a threaded screw portion including an enlarged head end and a head body. The threaded screw portion engages a pedicle of a vertebra of the spine, and the head body engages the threaded screw portion, optionally by passing the threaded screw portion down and through a hole manufactured into the bottom of the head body until the head end is seated in the bottom portion of the head body. The pedicle screws can be monoaxial or polyaxial, allowing the head body multiple degrees of freedom with respect to the threaded screw portion. Once placed, rods are inserted into the head bodies of adjacent pedicle screws and set screws are placed to simultaneously secure the head bodies to their respective threaded screw portions and to lock the rods in place. A rigid framework is thereby formed, stabilizing and fixing the vertebrae of the spine.

Typically, these pedicle screws are placed in a pre-assembled configuration, with the head body joined to the threaded screw portion. It is desirable, however, that a surgeon have a pedicle screw that may be placed in a substantially disassembled configuration, first placing the threaded screw portion, and then screwing the head body onto the threaded screw portion, at all times maintaining the polyaxial nature of the pedicle screw such that rods may be inserted as necessary before everything is locked together. The present invention provides such a pedicle screw.

BRIEF SUMMARY OF THE INVENTION

In various exemplary embodiments, the present invention provides a bone anchor, or pedicle screw, that includes a threaded screw portion including an externally threaded head end, an internally threaded head body, and an externally threaded compression saddle assembly. A rod is dropped into the head body on top of the compression saddle assembly and locked into place using a set screw. The head body can accommodate rod sizes between about 5.5 and 6 mm in diameter, for example. The bone anchor is polyaxial, such that the head body can rotate in a conical circle with respect to the threaded screw portion before it is locked into place by the rod and the set screw. The bone anchor can be pre-assembled in one piece before it is placed in a patient. Alternatively, the threaded screw portion can be placed in the patient minus the head body and the compression saddle assembly, which are assembled together. Once all of the threaded screw portions are placed, the compression saddle assemblies can be pre-assembled into the head bodies, and then the head bodies can be screwed onto the threaded screw portions, still maintaining their polyaxial nature.

In this latter methodology, the compression saddle assembly has external threads that engage internal threads manufactured into the hole in the bottom of the head body. The compression saddle assembly is screwed into the head body from the bottom until the compression saddle assembly passes into the interior portion of the head body and engages a stop structure manufactured therein. The head body is then placed on an insertion instrument that grips the outside of the head body and has a flat boss that engages the interior of the head body, such that the compression saddle assembly is held securely. The head body and compression saddle assembly are then screwed onto the externally threaded head end of the threaded screw portion that is already anchored in bone, via the internal threads of the head body. The mechanics of this engagement are described in greater detail herein below, as are all the components of the bone anchor. At this point, the head body still has sufficient rotation to allow the surgeon to place and manipulate the rods in the head bodies. The set screws are then placed. The tightening of the set screw then, through the rod, forces the compression saddle assembly down, and creates a compressive force therein. Via this compressive force, the compression saddle assembly secures the head body rigidly to the head end of the threaded screw portion, and the set screw secures the rod. This completes the assembly of the rigid construct.

Optionally, the screw thread form is between a cortical thread and a cancellous thread to provide maximum pullout strength. The set screw has a reverse square thread, for example, to prevent head splay after final tightening. The head body has cutouts on the sides to allow for the attachment of rod reducers, minimally invasive (MIS) instrumentation, and the like. Optionally, these cutouts have a 15 degree undercut to better grip the reduction and MIS instruments. Finally, the compression saddle assembly incorporates "wings" to prevent it from rotating within the head body. Again, all components of the bone anchor are described in greater detail herein below. It should be noted that all components of the bone anchor can be made of any suitable surgically implantable material, well known to those of ordinary skill in the art. Finally, a counterclockwise, or left hand, thread can be used to assemble the compression saddle assembly and threaded screw portion so as to prevent disassembly during threaded screw portion installation into bone, as the threaded screw portion typically utilizes a clockwise, or right hand, thread.

In one exemplary embodiment, the present invention provides a polyaxial bone anchor assembly, comprising: a threaded screw portion comprising an externally threaded head end; a head body selectively disposed concentrically about the externally threaded head end of the threaded screw portion, wherein the head body defines an internally threaded hole in a bottom portion thereof; and an externally threaded compression saddle assembly selectively disposed within an interior portion of the head body and selectively engaging the externally threaded head end of the threaded screw portion; wherein the externally threaded compression saddle assembly and the externally threaded head end of the threaded screw portion are selectively disposed within the interior portion of the head body by engaging and passing through the internally threaded hole in the bottom portion of the head body. The externally threaded compression saddle assembly is selectively compressed between a rod and the externally threaded head end of the threaded screw portion. The compression of the externally threaded compression saddle assembly between a rod and the externally threaded head end of the threaded screw portion secures the externally threaded head end of the threaded screw portion in a rigid orientation with respect to the head body. Optionally, the externally threaded compression saddle assembly comprises one or more longitudinal cuts manufactured therein that allow the externally threaded compression saddle assembly to be compressed between the rod and the externally threaded head end of the threaded screw portion. The head body comprises an internal stop structure that limits translation of the externally threaded compression saddle assembly within the interior portion of the head body. The internal stop structure prevents the externally threaded compression saddle assembly from translating through and out of a top portion of the head body. The rod is biased into the head body via a set screw.

In another exemplary embodiment, the present invention provides a polyaxial bone anchor method, comprising: providing a threaded screw portion comprising an externally threaded head end; providing a head body selectively disposed concentrically about the externally threaded head end of the threaded screw portion, wherein the head body defines an internally threaded hole in a bottom portion thereof; and providing an externally threaded compression saddle assembly selectively disposed within an interior portion of the head body and selectively engaging the externally threaded head end of the threaded screw portion; wherein the externally threaded compression saddle assembly and the externally threaded head end of the threaded screw portion are selectively disposed within the interior portion of the head body by engaging and passing through the internally threaded hole in the bottom portion of the head body. The externally threaded compression saddle assembly is selectively compressed between a rod and the externally threaded head end of the threaded screw portion. The compression of the externally threaded compression saddle assembly between a rod and the externally threaded head end of the threaded screw portion secures the externally threaded head end of the threaded screw portion in a rigid orientation with respect to the head body. Optionally, the externally threaded compression saddle assembly comprises one or more longitudinal cuts manufactured therein that allow the externally threaded compression saddle assembly to be compressed between the rod and the externally threaded head end of the threaded screw portion. The head body comprises an internal stop structure that limits translation of the externally threaded compression saddle assembly within the interior portion of the head body. The internal stop structure prevents the externally threaded compression saddle assembly from translating through and out of a top portion of the head body. The rod is biased into the head body via a set screw. The method comprises disposing the threaded screw portion in a bone of a patient. Optionally, the method comprises subsequently coupling the heady body and the externally threaded compression saddle assembly to the threaded screw portion.

In a further exemplary embodiment, the present invention provides a polyaxial bone anchor retention and placement instrument, comprising: an elongate shaft portion comprising a proximal end and a distal end; a head body retention assembly coupled to the proximal end of the elongate shaft portion, wherein the head body retention assembly comprises a pair of opposed elongate structures configured to selectively engage a corresponding pair of opposed recesses manufactured into an exterior or interior portion of a head body of a polyaxial bone anchor, and wherein the head body retention assembly further comprises a central boss or shaft structure that selectively protrudes into an interior portion of the head body and contacts a saddle assembly disposed therein; and a handle portion coupled to the distal end of the elongate shaft portion. Each of the pair of opposed elongate structures comprises an internal or external protrusion that is configured to selectively engage the corresponding recess manufactured into the exterior or interior portion of the head body. Optionally, the head body retention assembly is coupled to the head body and contacts the saddle assembly while the head body and saddle assembly are coupled to a head end of a threaded screw portion of the polyaxial bone anchor.

BRIEF DESCRIPTION OF THE DRAWINGS

The present invention is illustrated and described herein with reference to the various drawings, in which like reference numbers are used to refer to like assembly components, and in which.

DETAILED DESCRIPTION OF THE INVENTION

Figure 1:
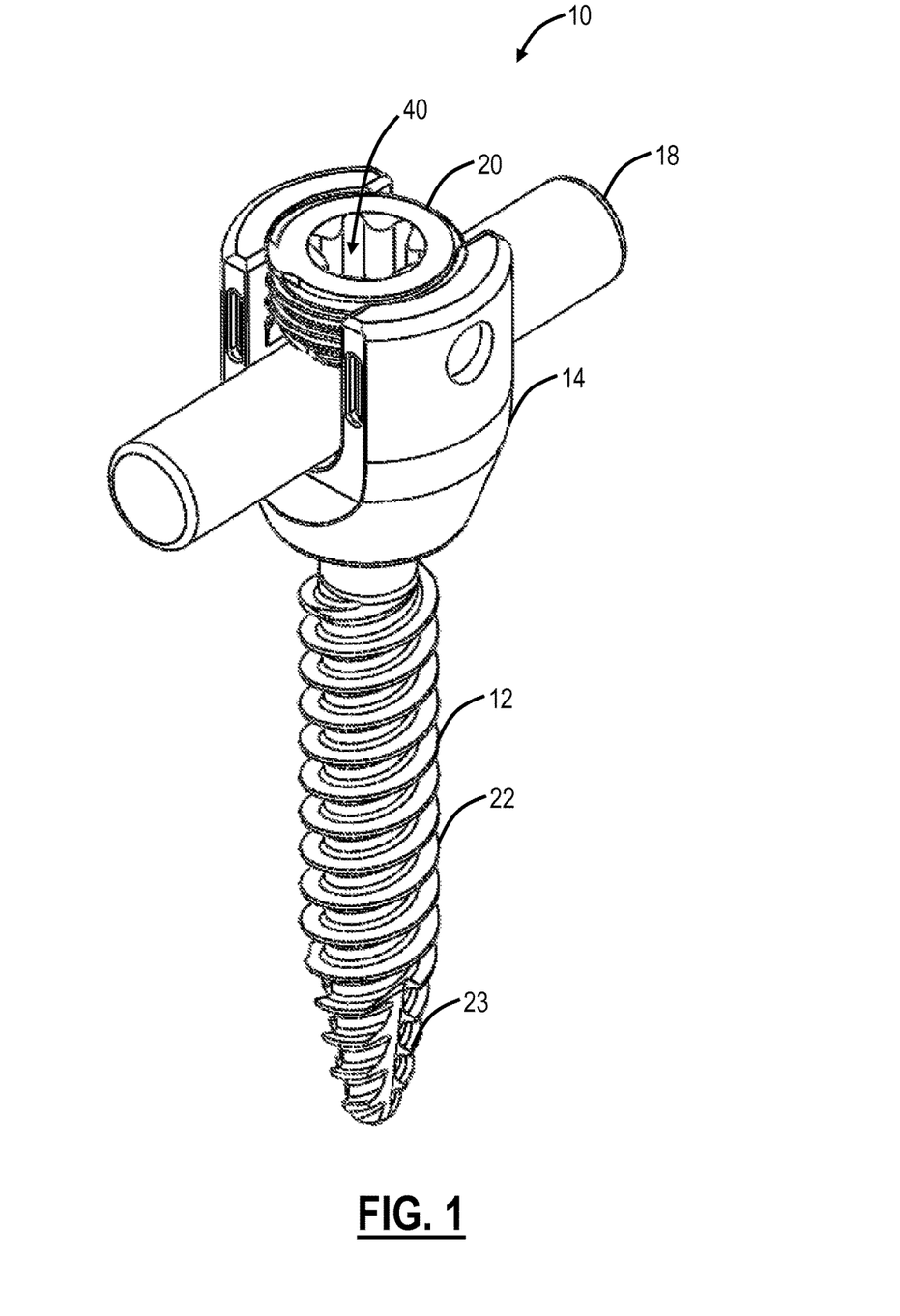
FIG. 1 is a perspective view of one exemplary embodiment of the bone anchor of the present invention in an assembled configuration, including the placement and retention of a rod and a set screw.
Figure 2:
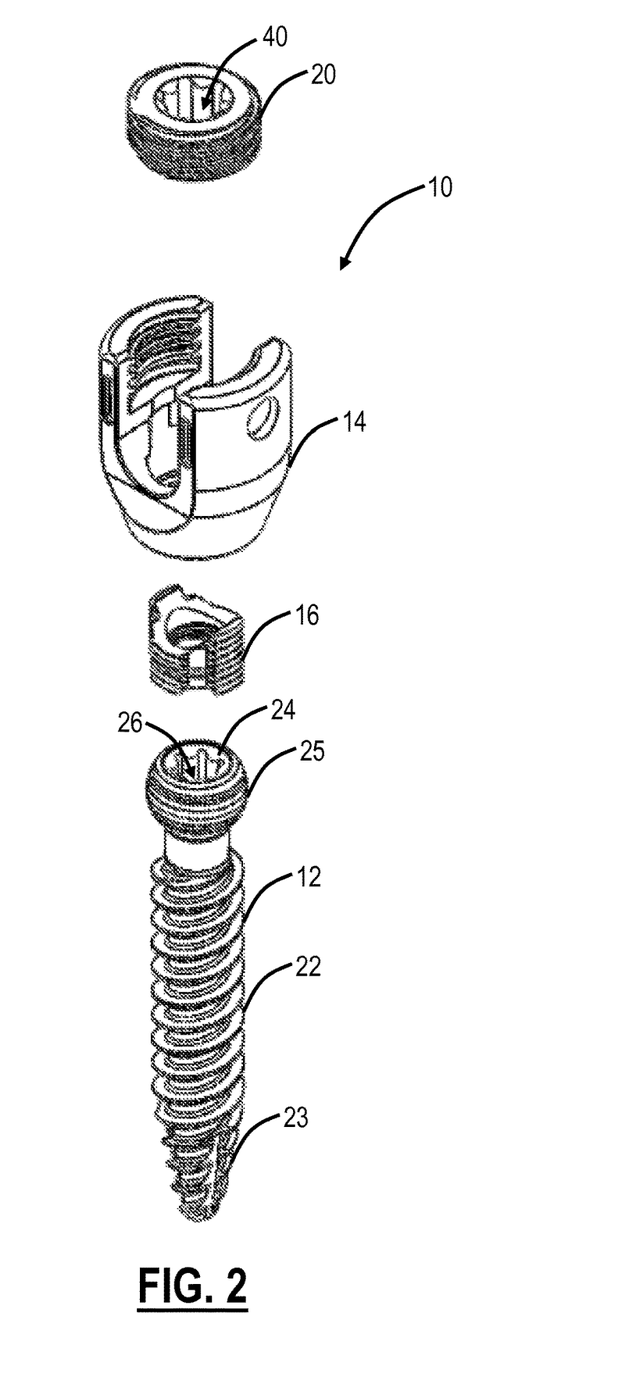
FIG. 2 is a perspective view of one exemplary embodiment of the bone anchor of the present invention in a disassembled configuration.

Referring now specifically to FIGS. 1 and 2, in one exemplary embodiment, the present invention provides a bone anchor 10, or pedicle screw, that includes a threaded screw portion 12, a head body 14, and a compression saddle assembly 16 (FIG. 2). When assembled, a rod 18 (FIG. 1) is dropped into the head body 14 on top of the compression saddle assembly 16 and locked into place using a set screw 20. The head body 14 can accommodate rod sizes between about 5.5 and 6 mm in diameter, for example. Optionally, the screw thread form is between a cortical thread and a cancellous thread to provide maximum pullout strength. The set screw 20 has a reverse square thread, for example, to prevent head splay after final tightening. The bone anchor 10 is polyaxial, such that the head body 14 can rotate in a conical circle with respect to the threaded screw portion 12 before it is locked into place by the rod 18 and the set screw 20. As described herein above and in greater detail herein below, the bone anchor 10 can be pre-assembled in one piece before it is placed in a patient. Alternatively, the threaded screw portion 12 can be placed in the patient minus the head body 14 and the compression saddle assembly 16, which are assembled together. Once all of the threaded screw portions 12 are placed, the compression saddle assemblies 16 can be pre-assembled into the head bodies 14, and then the head bodies 14 can be screwed onto the threaded screw portions 12, still maintaining their polyaxial nature. Again, it should be noted that all components of the bone anchor 10 can be made of any suitable surgically implantable material, well known to those of ordinary skill in the art.

The threaded screw portion 12 includes a threaded shaft portion 22 and a threaded tapered end portion 23 that collectively engage and affix the threaded screw portion 12 to the target bone, as with conventional pedicle screws. The threaded screw portion 12 also includes a head end 24 (FIG. 2) including a recessed driver receptacle 26 (FIG. 2) that is configured to receive a driver instrument for driving the threaded screw portion 12 into the target bone. Again, this is similar to conventional pedicle screws. In this exemplary embodiment, the head end 24 includes external threads 25 configured to selectively engage the head body 14.

Figure 3:
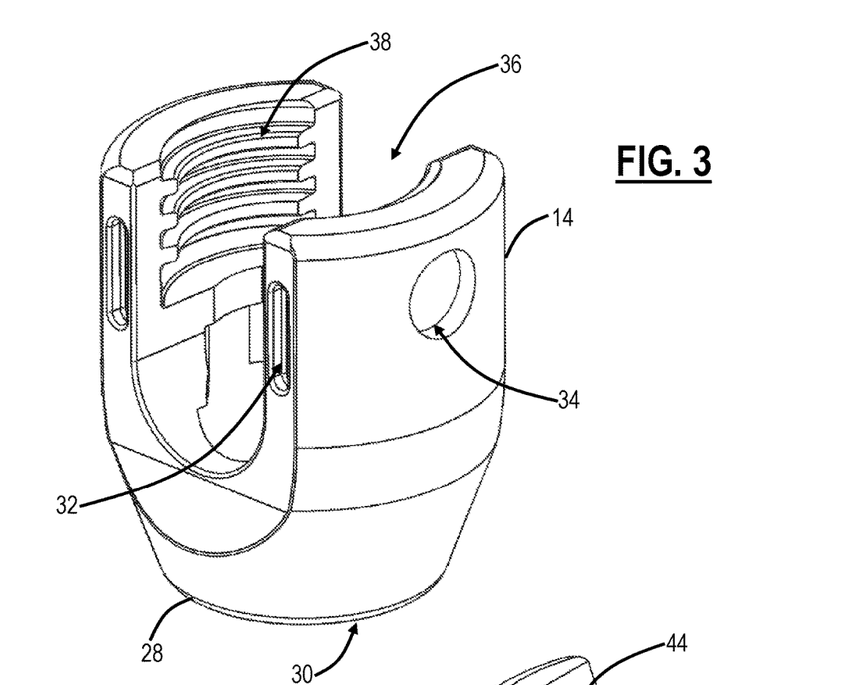
FIG. 3 is a perspective view of one exemplary embodiment of the head body of the bone anchor of the present invention.

Referring now specifically to FIG. 3, in one exemplary embodiment, the head body 14 has a generally cylindrical shape with a partially closed and, optionally, tapered bottom portion 28. This bottom portion 28 defines an internally threaded hole 30 into which the head end 24 (FIG. 2) of the threaded screw portion 12 (FIGS. 1 and 2) is screwed, allowing the head end 24 of the threaded screw portion 12 to be drawn and pass into the interior portion of the head body 14. The head body 14 includes any number and/or configuration of cutouts 32, 34 for receiving retention and placement instrumentation, reduction and MIS instruments, etc. Specifically, in this exemplary embodiment, the head body 14 includes cutouts 34 for receiving an insertion instrument, described herein above and in greater detail herein below, that grips the outside of the head body 14 and has a flat boss that engages the interior of the head body 14, such that the compression saddle assembly 16 (FIG. 2) is oriented and stabilized within the head body 14. Optionally, these cutouts 32, 34 have a 15 degree undercut to better grip the retention, placement, reduction, and MIS instruments. The head body 14 further includes a pair of opposed recesses 36 that are configured to receive the rod 18 (FIG. 1) into/through the head body 14. Finally, the head body 14 includes internal threading 38 that is configured to receive and retain the externally threaded set screw 20 (FIG. 1), which of course includes a recessed driver receptacle 40 (FIGS. 1 and 2) that is configured to receive a driver instrument for screwing the set screw 20 into the head body 14. Again, this is similar to conventional pedicle screws.

Figure 4:
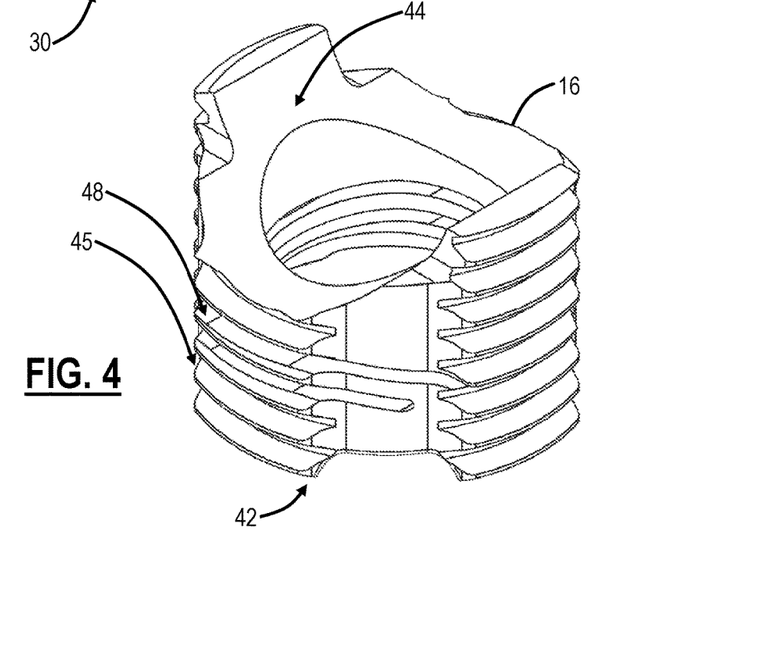
FIG. 4 is a perspective view of one exemplary embodiment of the compression saddle assembly of the bone anchor of the present invention.

Referring now specifically to FIG. 4, in one exemplary embodiment, the compression saddle assembly 16 has a generally cylindrical shape and, when assembled, sits inside of the head body 14 (FIGS. 1-3). A plurality of wing like protrusions 42 extend concentrically outward from the sides of the compression saddle assembly 16 and engage the rod recesses 36 (FIG. 3) of the head body 14, such that rotation of the compression saddle assembly 16 within the head body 14 is prevented. In general, the saddle assembly 16 is allowed to travel up and down slightly within the head body 14, such that the position of the compression saddle assembly 16 within the head body 14 can be adjusted. The compression saddle assembly 16 also includes a recess 44 that is configured to receive and orient the rod 18 (FIG. 1) when placed. The compression saddle assembly 16 further includes external threads 45 that are configured to engage the internally threaded hole 30 (FIG. 3) in the bottom portion 28 (FIG. 3) of the head body 14, thereby drawing the compression saddle assembly into the interior portion of the head body, where the compression saddle is retained. These various threads loosely bring the threaded screw portion 12 (FIGS. 1 and 2), the head body 14, and the compression saddle assembly 16 together, as is described in greater detail herein below, with the head end 24 (FIG. 2) of the threaded screw portion 12 and the compression saddle assembly 16 being disposed within the interior portion of the head body 14. The threaded screw portion is unable to pass back out of the head body and the compression saddle assembly 16 is unable to pass through the top portion of the head body 14.

Figure 5:
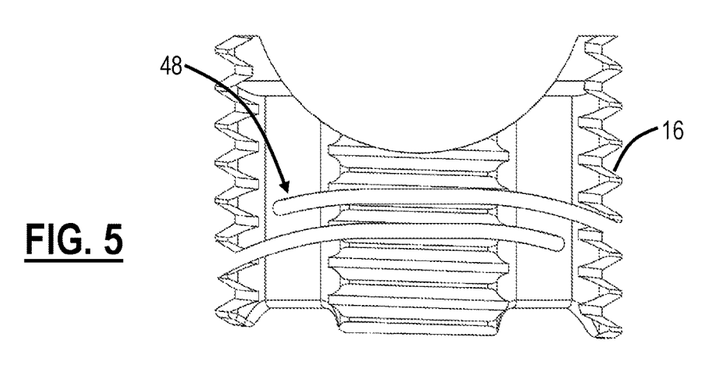
FIG. 5 is a cross-sectional side view of one exemplary embodiment of the compression saddle assembly of the bone anchor of the present invention.

Referring now specifically to FIG. 5, in one exemplary embodiment, the bottom portion of the compression saddle assembly 16 is sized and shaped such that it substantially conforms to the size and shape of the head end 24 (FIG. 2) of the threaded screw portion 12 (FIGS. 1 and 2). In this exemplary embodiment, the head end 24 of the threaded screw portion 12 has a substantially circular or elliptical shape, although it will be readily apparent to those of ordinary skill in the art that other suitable shapes can be utilized. In this manner, the compression saddle assembly 16 snugly engages the head end 24 of the threaded screw portion 12. The compression saddle assembly 16 includes one or more longitudinal cuts 48 that allow the compression saddle assembly to be compressed slightly, and exert a compressive force, between the rod 18 (FIG. 1) and the head end 24 of the threaded screw portion 12, thereby selectively locking all of the components together.

Figure 6:
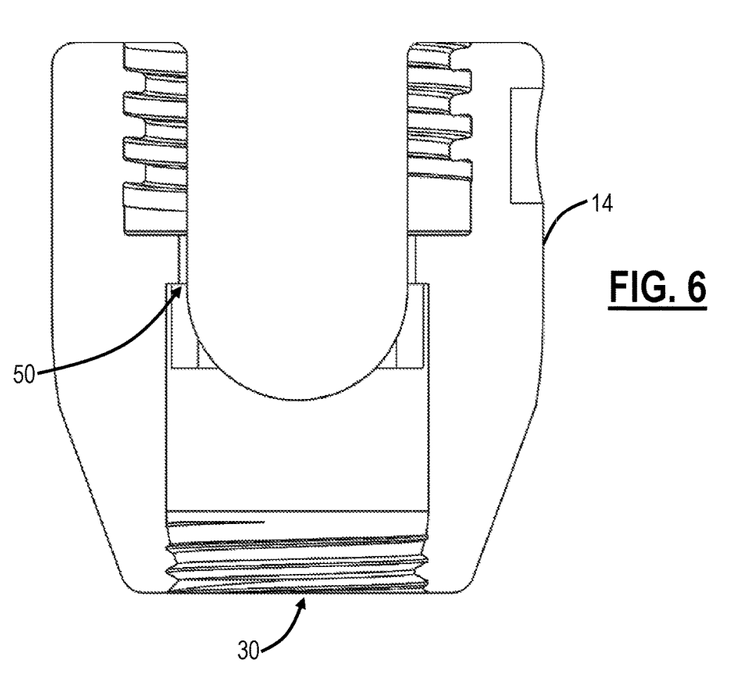
FIG. 6 is a cross-sectional side view of one exemplary embodiment of the head body of the bone anchor of the present invention.
Figure 7:
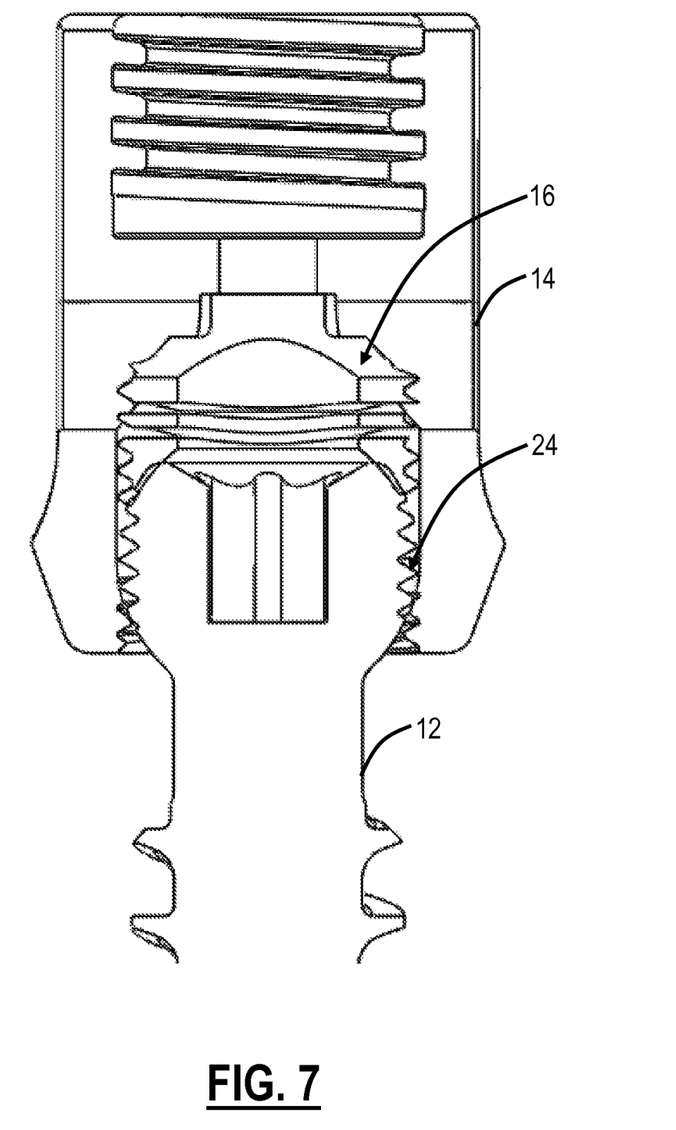
FIG. 7 is a cross-sectional side view of one exemplary embodiment of the bone anchor of the present invention in an assembled configuration, minus the placement and retention of the rod and the set screw.

Referring now specifically to FIG. 6, in one exemplary embodiment, the interior portion of the head body 14 utilizes the internally threaded hole 30 and a plurality of different internal diameters that, along with a shoulder structure 50, form an internal volume in which the compression saddle assembly 16 (FIGS. 2, 4, and 5) and head end 24 (FIG. 2) are retained once they are threaded through the internally threaded hole 30 of the head body 14. During assembly, for example, the compression saddle assembly 16 is screwed into the head body 14, where it "slides" into place beneath the shoulder structure 50. This is the first position for the compression saddle assembly 16. The head body 14 is then placed on an insertion instrument that grips the outside of the head body 14 and has a flat boss that engages the interior of the head body 14, such that the saddle assembly 16 is oriented and stabilized within the head body 14. The head body 14 and compression saddle assembly 16 are then screwed onto the head end 24 of the threaded screw portion (FIGS. 1 and 2) that is already anchored in bone. At this point, the head body 14 still has sufficient rotation to allow the surgeon to place and manipulate the rods 18 (FIG. 1) in the head bodies 14. The set screws 20 (FIGS. 1 and 2) are then placed. The tightening of the set screw 20 then, through the rod 18, forces the compression saddle assembly 16 down and into compression, such that it compresses the head end 24 of the threaded screw portion against the bottom portion 28 (FIG. 3) of the head body 14. In this second position, the compression saddle assembly 16 secures the head body 14 rigidly to the head end 24 of the threaded screw portion 12, and the set screw 20 secures the rod 18. This completes the assembly of the rigid construct, with the head end 24 of the threaded screw portion 12 snugly engaging the compression saddle assembly 16, and the compression saddle assembly 16 being secured in the second position within the head body 14. This assembled configuration is further illustrated in FIG. 7.

Figure 8:
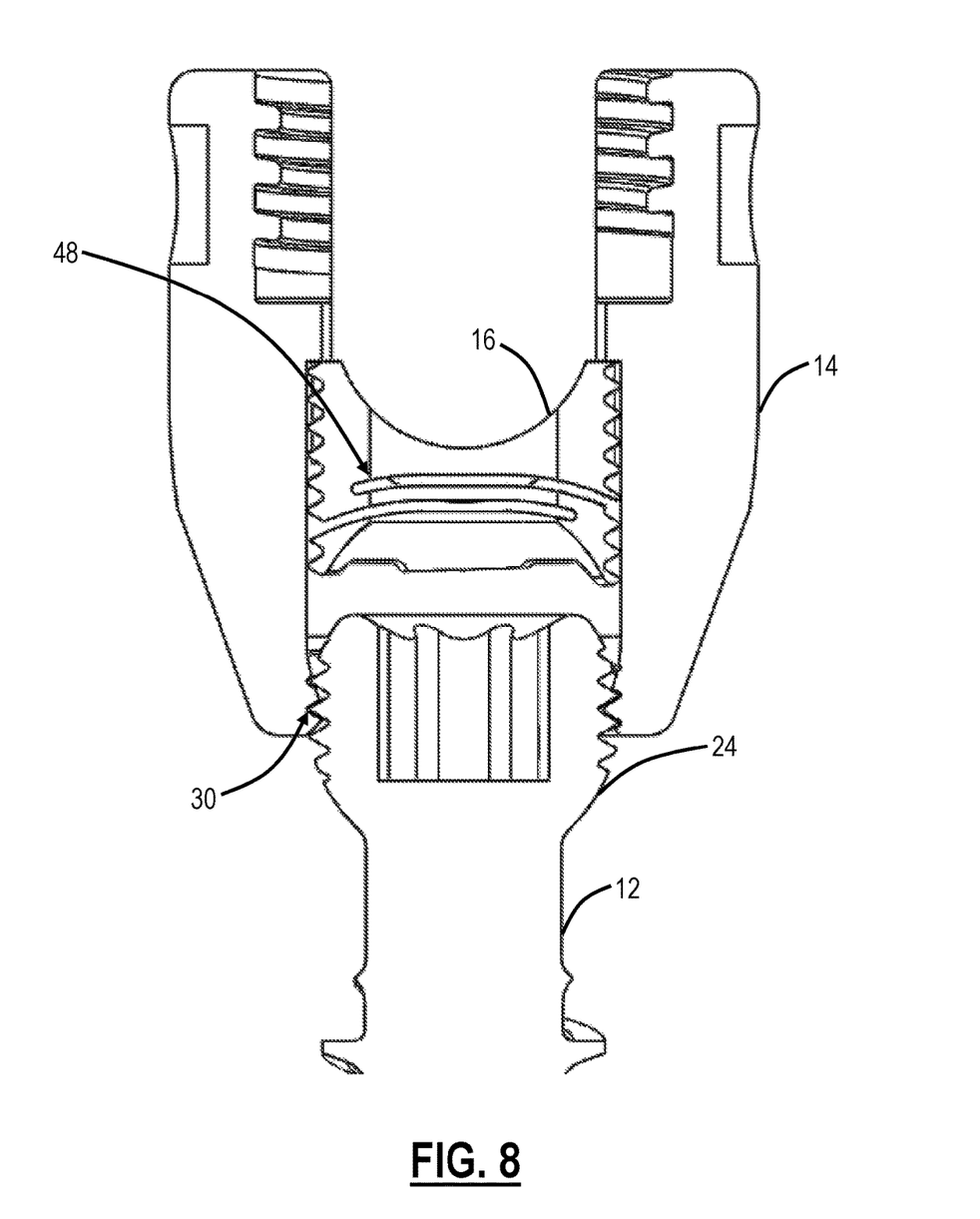
FIG. 8 is a partial cross-sectional side view of one exemplary embodiment of the bone anchor of the present invention in an assembled configuration, minus the placement and retention of the rod and the set screw.

Referring now specifically to FIG. 8, in one exemplary embodiment, the compression saddle assembly 16 is disposed in the first position, with the head end 24 of the threaded screw portion 12 being screwed into the head body 14 to engage the compression saddle assembly 16. In this configuration, once the head end 24 of the threaded screw portion 12 passes into the interior portion of the head body 14, the head body 14 is still free to move with respect to the threaded screw portion 12. Thus, the head end 24 of the threaded screw portion 12 is screwed into and passes the threaded hole 30 of the head body 14, allowing the head end 24 of the threaded screw portion 12 to spherically articulate within the head body 14.

Figure 9:
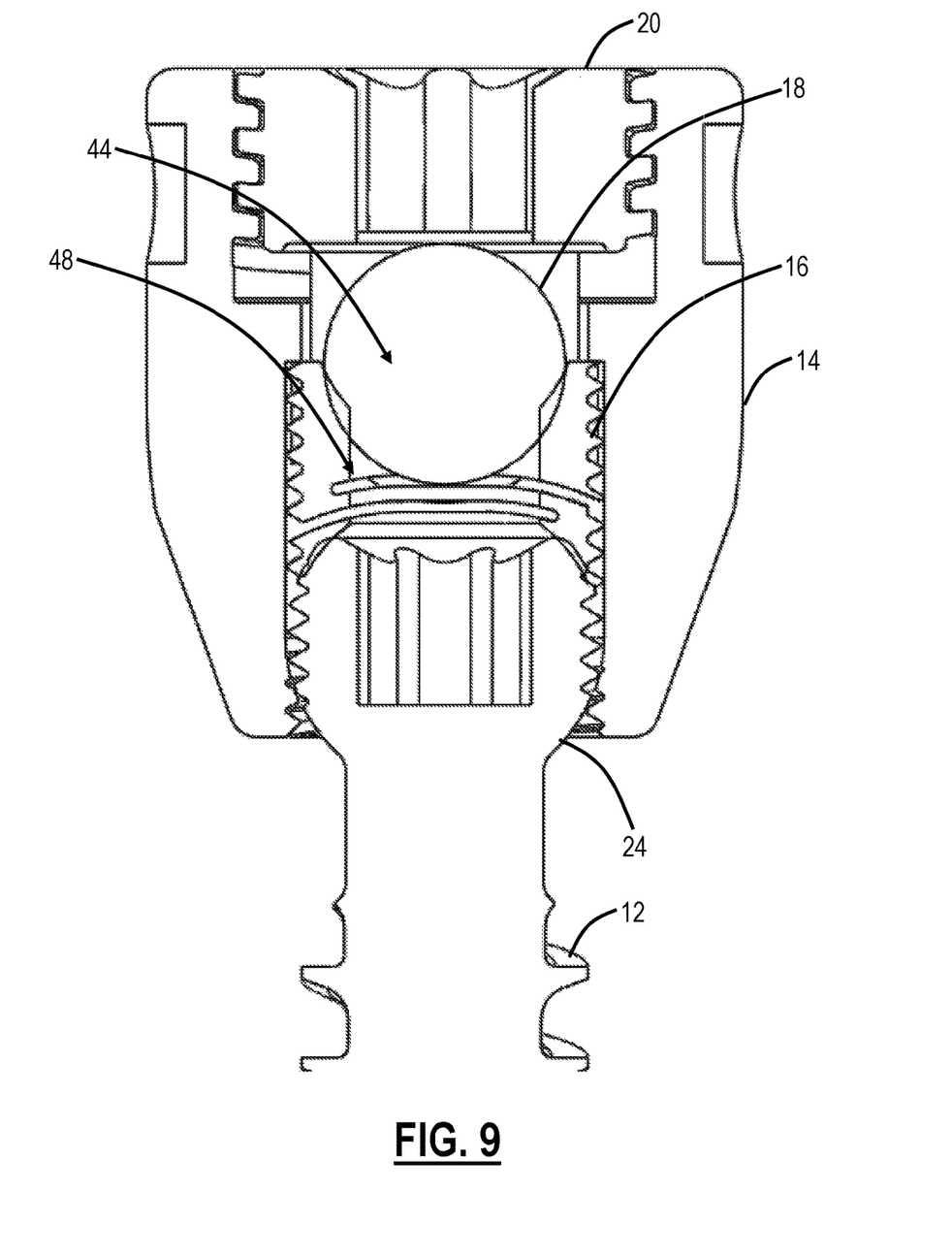
FIG. 9 is a partial cross-sectional side view of one exemplary embodiment of the bone anchor of the present invention in an assembled configuration, including the placement and retention of the rod and the set screw.

Referring now specifically to FIG. 9, in one exemplary embodiment, the compression saddle assembly 16 is driven into the second position via tightening of the set screw 20 and the deflection of the rod 18 deeper into the head body 14, with the head end 24 of the threaded screw portion 12 engaging the conforming bottom surface of the compression saddle assembly 16, which now exerts a compressive force on the various components. It should be noted that the rod 18 sits in the corresponding recess 44 of the compression saddle assembly 16. In this configuration, the head body 14 is secured with respect to the threaded screw portion 12. The rod 18 is also locked firmly into place.

Figure 10:
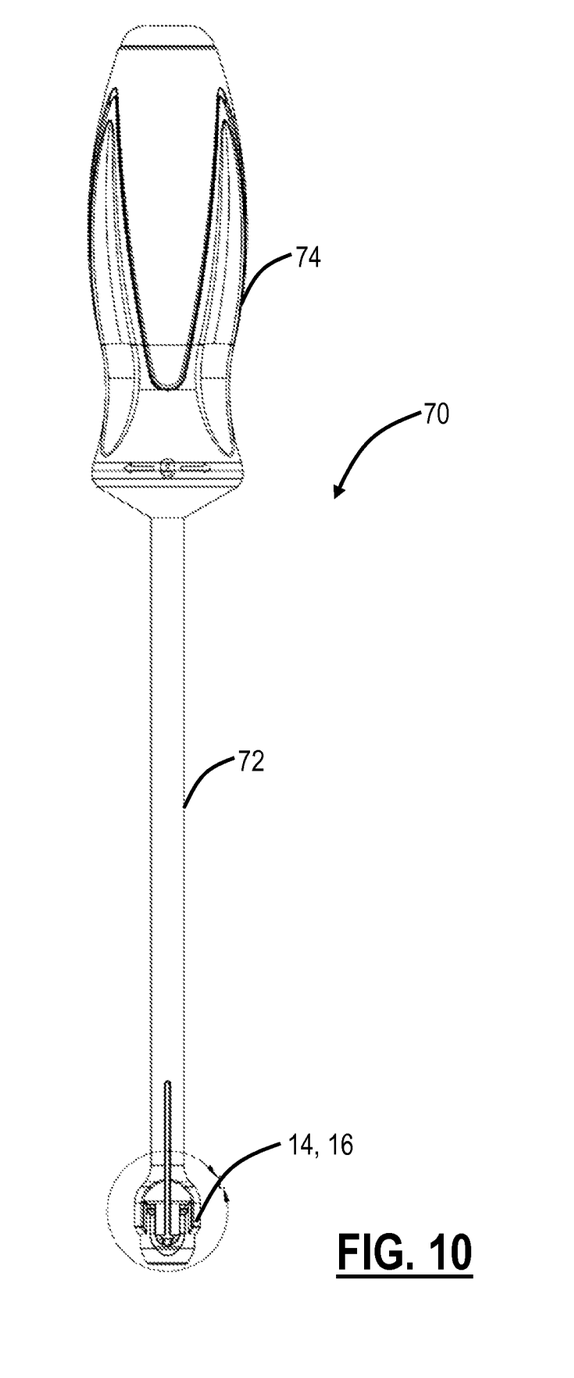
FIG. 10 is a side view of one exemplary embodiment of the head body retention and placement instrument of the present invention, with an engaged head body and compression saddle assembly.

Referring now specifically to FIG. 10, in one exemplary embodiment, the head body retention and placement instrument 70—includes an elongate shaft portion 72. The head body 14 and compression saddle assembly 16 are selectively coupled to a proximal end of the elongate shaft portion 72. A distal end of the elongate shaft portion 72 includes a handle portion 74, by which the instrument is manipulated.

Figure 11:
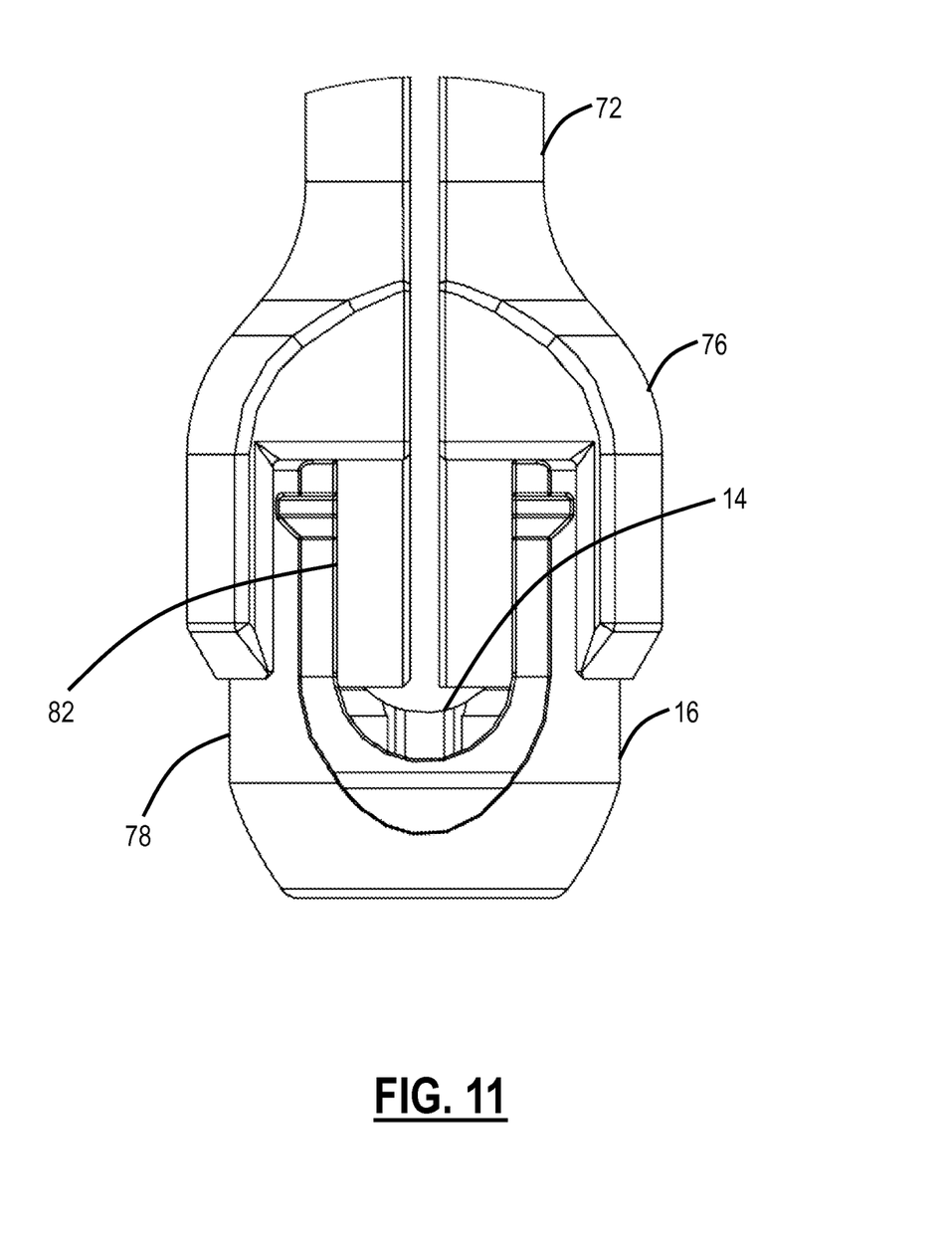
FIG. 11 is a partial cross-sectional side view of one exemplary embodiment of the head body retention and placement instrument of the present invention, with the engaged head body and compression saddle assembly.

Referring now specifically to FIGS. 10 and 11, in one exemplary embodiment, the proximal end of the elongate shaft portion 72 includes a pair of elongate structures 76 (FIG. 11) that selectively engage elongate sides 78 (FIG. 11) of the head body 14. As alluded to previously, the elongate structures 76 can each include an interior protruding portion that engages the corresponding recess 34 (FIG. 3) manufactured into the outside of each of the elongate sides 78 of the head body 14. Using this mechanism, the instrument can be "snapped" onto and "snapped" off of the head body 14, and thereby used to screw the head body 14 and compression saddle assembly 16 onto the head end 24 (FIGS. 2 and 7-9) of the threaded screw portion 12 (FIGS. 1, 2, and 7-9). The proximal end of the elongate shaft portion 72 includes a central boss 82 (FIG. 11) that is disposed within the interior portion of the head body 14 and abuts the flat upper surface of the compression saddle assembly 16, thereby orienting and stabilizing the compression saddle assembly 16 within the head body 14 during bone anchor assembly.

As described herein above, the present invention provides a bone anchor 10, or pedicle screw, that includes a threaded screw portion 12 including an externally threaded head end 24, an internally threaded head body 14, and an externally threaded compression saddle assembly 16. A rod 18 is dropped into the head body 14 on top of the compression saddle assembly 16 and locked into place using a set screw 20. The head body 14 can accommodate rod sizes between about 5.5 and 6 mm in diameter, for example. The bone anchor 10 is polyaxial, such that the head body 14 can rotate in a conical circle with respect to the threaded screw portion 12 before it is locked into place by the rod 18 and the set screw 20. The bone anchor 10 can be pre-assembled in one piece before it is placed in a patient. Alternatively, the threaded screw portion 12 can be placed in the patient minus the head body 14 and the compression saddle assembly 16, which are assembled together. Once all of the threaded screw portions 12 are placed, the compression saddle assemblies 16 can be pre-assembled into the head bodies 14, and then the head bodies 14 can be screwed onto the threaded screw portions 12, still maintaining their polyaxial nature.

In this latter methodology, the compression saddle assembly 16 has external threads 45 that engage internal threads manufactured into the hole 30 in the bottom of the head body 14. The compression saddle assembly 16 is screwed into the head body 14 from the bottom until the compression saddle assembly 16 passes into the interior portion of the head body 14 and engages a stop structure 50 manufactured therein. The head body 14 is then placed on an insertion instrument 70 that grips the outside of the head body 14 and has a flat boss 82 that engages the interior of the head body 14, such that the compression saddle assembly 16 is held securely. The head body 14 and compression saddle assembly 16 are then screwed onto the externally threaded head end 24 of the threaded screw portion 12 that is already anchored in bone, via the internal threads 38 of the head body 14. At this point, the head body 14 still has sufficient rotation to allow the surgeon to place and manipulate the rods 18 in the head bodies 14. The set screws 20 are then placed. The tightening of the set screw 20 then, through the rod 18, forces the compression saddle assembly 16 down, and creates a compressive force therein. Via this compressive force, the compression saddle assembly 16 secures the head body 14 rigidly to the head end 24 of the threaded screw portion 12, and the set screw 20 secures the rod 18. This completes the assembly of the rigid construct.

Optionally, the screw thread form is between a cortical thread and a cancellous thread to provide maximum pullout strength. The set screw 20 has a reverse square thread, for example, to prevent head splay after final tightening. The head body 14 has cutouts 32, 34 on the sides to allow for the attachment of rod reducers, minimally invasive (MIS) instrumentation, and the like. Optionally, these cutouts 32, 34 have a 15 degree undercut to better grip the reduction and MIS instruments. Finally, the compression saddle assembly 16 incorporates "wings" 42 to prevent it from rotating within the head body 14. It should be noted that all components of the bone anchor 10 can be made of any suitable surgically implantable material, well known to those of ordinary skill in the art. Finally, a counterclockwise, or left hand, thread can be used to assemble the compression saddle assembly 16 and threaded screw portion 12 so as to prevent disassembly during threaded screw portion 12 installation into bone, as the threaded screw portion 12 typically utilizes a clockwise, or right hand, thread.

Although the present invention is illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the present invention, are contemplated thereby, and are intended to be covered by the following non-limiting claims.

What is claimed is:

1. A polyaxial bone anchor assembly, comprising:
   a threaded screw portion comprising an externally threaded head end;
   a head body selectively disposed concentrically about the externally threaded head end of the threaded screw portion, wherein the head body defines an internally threaded hole in a bottom portion thereof; and
   an externally threaded compression saddle assembly selectively disposed within an interior portion of the head body by threadingly engaging and passing through the internally threaded hole in the bottom portion of the head body and selectively engaging the externally threaded head end of the threaded screw portion, wherein the externally threaded compression saddle defines a plurality of convex longitudinal cuts that cause the externally threaded compression saddle to be compressed between both an internal stop structure manufactured into the interior portion of the head body and a rod and the externally threaded head end of the threaded screw portion, and wherein adjacent convex longitudinal cuts are open to opposed sides of the externally threaded compression saddle;
   wherein both the externally threaded compression saddle assembly and the externally threaded head end of the threaded screw portion are selectively disposed within the interior portion of the head body by threadingly engaging and passing through the internally threaded hole in the bottom portion of the head body; and
   wherein the internal stop structure that limits translation of the externally threaded compression saddle assembly within the interior portion of the head body, the entire externally threaded compression saddle assembly disposed beneath the internal stop structure.

2. The polyaxial bone anchor assembly of claim 1, wherein the compression of the externally threaded compression saddle assembly between the rod and the externally threaded head end of the threaded screw portion secures the externally threaded head end of the threaded screw portion in a rigid orientation with respect to the head body.

3. The polyaxial bone anchor assembly of claim 1, wherein the internal stop structure prevents the externally threaded compression saddle assembly from translating through and out of a top portion of the head body.

4. The polyaxial bone anchor assembly of claim 1, wherein the rod is biased into the head body via a set screw.

* * * * *